(12) United States Patent
March

(10) Patent No.: US 6,850,786 B2
(45) Date of Patent: *Feb. 1, 2005

(54) OCULAR ANALYTE SENSOR

(75) Inventor: Wayne Front March, Galveston, TX (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/655,502

(22) Filed: Sep. 3, 2003

(65) Prior Publication Data

US 2004/0059207 A1 Mar. 25, 2004

Related U.S. Application Data

(63) Continuation of application No. 09/784,471, filed on Feb. 15, 2001, now Pat. No. 6,681,127, which is a continuation-in-part of application No. PCT/EP00/08285, filed on Aug. 24, 2000.
(60) Provisional application No. 60/185,980, filed on Mar. 1, 2000, and provisional application No. 60/150,792, filed on Aug. 26, 1999.

(51) Int. Cl.[7] .................................................. A61B 5/00
(52) U.S. Cl. ...................................... 600/321; 600/319
(58) Field of Search ................................ 600/319, 318, 600/321, 322, 329, 317

(56) References Cited

U.S. PATENT DOCUMENTS

| | | | |
|---|---|---|---|
| 3,769,961 A | 11/1973 | Fatt et al. .................. 128/2 T |
| 4,330,299 A | 5/1982 | Cerami ........................ 23/230 |
| 4,344,438 A | 8/1982 | Schultz ........................ 128/634 |
| 5,222,495 A | 6/1993 | Clarke et al. ................ 128/633 |
| 5,246,867 A | 9/1993 | Lakowicz et al. ............ 436/95 |
| 5,263,992 A | 11/1993 | Guire ........................... 623/66 |
| 5,341,805 A | 8/1994 | Stavridi et al. ............. 128/633 |
| 5,342,789 A | 8/1994 | Chick et al. ................. 436/501 |
| 5,352,411 A | 10/1994 | Khuri .......................... 422/58 |

(List continued on next page.)

FOREIGN PATENT DOCUMENTS

| | | |
|---|---|---|
| EP | 0 236 023 | 9/1987 |
| SU | 1534406 A1 | 1/1990 |
| WO | WO 93/01745 | 2/1993 |
| WO | WO 97/19188 | 5/1997 |
| WO | WO 98/22820 | 5/1998 |
| WO | WO 99/51142 | 10/1999 |
| WO | WO 00/10007 | 2/2000 |
| WO | WO 00/13580 | 3/2000 |
| WO | WO 00/16099 | 3/2000 |
| WO | WO 00/64492 | 11/2000 |
| WO | WO 01/18237 A1 | 3/2001 |
| WO | WO 02/03855 | 1/2002 |

OTHER PUBLICATIONS

TV News Reports.
Technology News: MSNBC.COM "Contact Lens Measures Glucose".

(List continued on next page.)

Primary Examiner—Eric F. Winakur
Assistant Examiner—Matthew Kremer
(74) Attorney, Agent, or Firm—Jian Zhou; Robert J. Gorman; R. Scott Meece

(57) ABSTRACT

An ophthalmic lens comprising a receptor moiety can be used to determine the amount of an analyte in an ocular fluid. The receptor moiety can bind either a specific analyte or a detectably labeled competitor moiety. The amount of detectably labeled competitor moiety which is displaced from the receptor moiety by the analyte is measured and provides a means of determining analyte concentration in an ocular fluid, such as tears, aqueous humor, or interstitial fluid. The concentration of the analyte in the ocular fluid, in turn, indicates the concentration of the analyte in a fluid or tissue sample of the body, such as blood or intracellular fluid.

22 Claims, 5 Drawing Sheets

U.S. PATENT DOCUMENTS

| | | | |
|---|---|---|---|
| 5,356,780 A | 10/1994 | Robinson et al. | 435/7.6 |
| 5,383,452 A | 1/1995 | Buchert | 128/633 |
| 5,433,197 A | 7/1995 | Stark | 128/633 |
| 5,503,770 A | 4/1996 | James et al. | 252/301.16 |
| 5,711,915 A | 1/1998 | Siegmund et al. | 422/68.1 |
| 5,820,557 A | 10/1998 | Hattori et al. | 600/319 |
| 5,830,139 A | 11/1998 | Abreu | 600/405 |
| 5,898,004 A | 4/1999 | Asher et al. | 436/518 |
| 6,011,984 A | 1/2000 | Van Antwerp et al. | 600/317 |
| 6,040,194 A | 3/2000 | Chick et al. | 436/501 |
| 6,120,460 A | 9/2000 | Abreu | 600/558 |
| 6,152,875 A | 11/2000 | Hakamata | 600/319 |
| 6,187,599 B1 | 2/2001 | Asher et al. | 436/531 |
| 6,197,534 B1 | 3/2001 | Lakowicz et al. | 435/14 |
| 6,197,928 B1 | 3/2001 | Tsien et al. | 530/350 |
| 6,312,393 B1 | 11/2001 | Abreu | 600/558 |
| 6,319,540 B1 | 11/2001 | Van Antwerp et al. | 427/2.13 |
| 6,366,793 B1 * | 4/2002 | Bell et al. | 600/317 |
| 6,540,895 B1 * | 4/2003 | Spence et al. | 204/450 |
| 6,681,127 B2 * | 1/2004 | March | 600/319 |

OTHER PUBLICATIONS

Lundgren et al., "A Dynamical Investigation of Acrylodan–Labeled Mutant Phosphate Binding Protein", Analytical Chemistry, 71 (3), 589–595 (1999).

Komives et al., "Improvement of Optical Fiber Based Biosensors", Annual International Conference of the IEEE Engineering in Medicine and Biology Society, vol. 12, No.2, 478–479 (1990).

Schauer–Vukasinovic et al., Rational Design of a Calcium Sensing System on Induced Conformational Changes of Calmodium, Journal of the American Chemical Society, vol. 119, No. 45, 11102–11103 (1997).

Schultz et al., "Affinity Sensors for Individual Metabolites", Biotechnology and Bioengineering Symp No. 9, 65–71 (1979).

Schultz et al., "Affinity Sensor: A New Technique for Developing Implantable Sensors for Glucose and other Metabolites", Diabetes Care, vol. 5 No. 3, May–Jun. 245–253 (1982).

Meadows et al., "Fiber–Optic Biosensors Based on Fluorescence Energy Transfer", Talanta, vol. 35, No. 2, 145–150 (1988).

The Photonics Dictionary, 1996 Book 4, 42nd Edition, pp. D24, D153.

Manual of Skin Diseases, Fifth Edition, Gordon C. Sauer, Md., 1985, pp. 204, 373.

Fm–2 Fluorotron Master Ocular Fluorophotometer, 1994 OcuMetrics, Inc.

Textbook of BioChemistry With Clinical Correlations, Second Edition, Thomas M. Devlin, Ph.D., 1986, pp. 118, 139.

Physical Optics, Third Revised Edition, RObert W. Wood, 1961, pp. 650–651.

Salins et al., "Optical Sensing System for Glucose Based on Genetically Engineered Galactose / Glucose Binding Protein", Pitcon '99 Book of Abstracts, Mar. 7–12, 747.

Aylott et al., "Development of Fiber Optic Based Glucose Biosensors", Pitcon '99 Book of Abstracts, Mar. 7–12, 748.

* cited by examiner

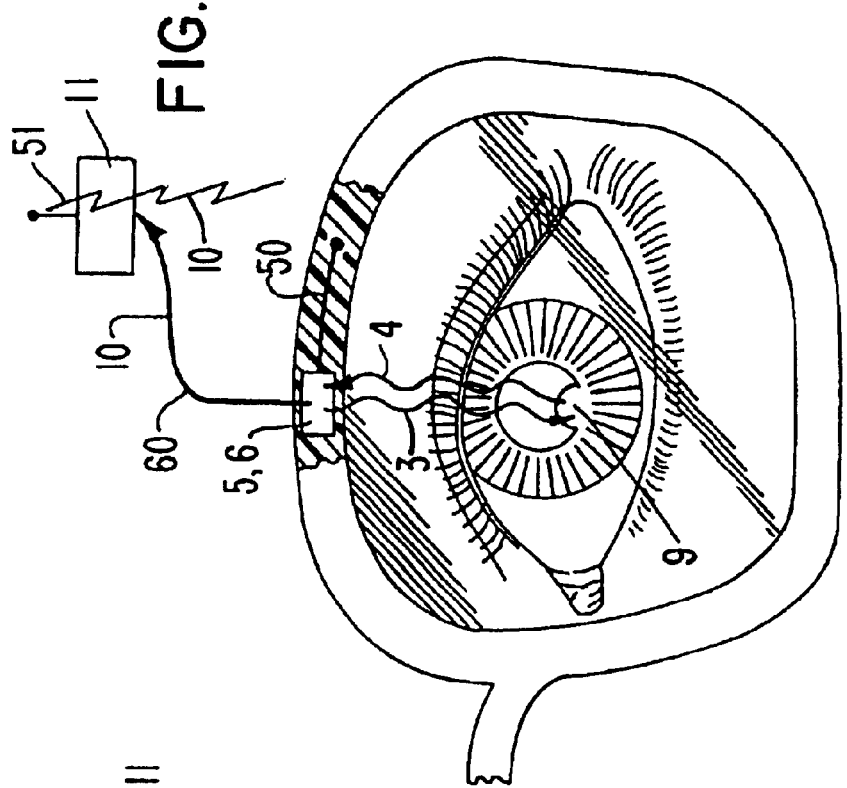
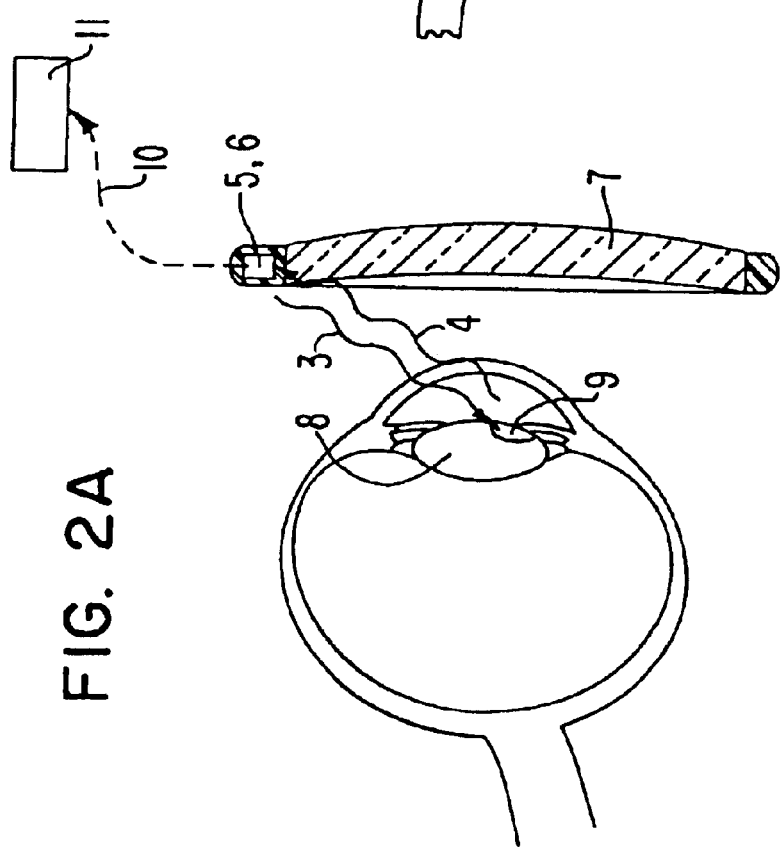

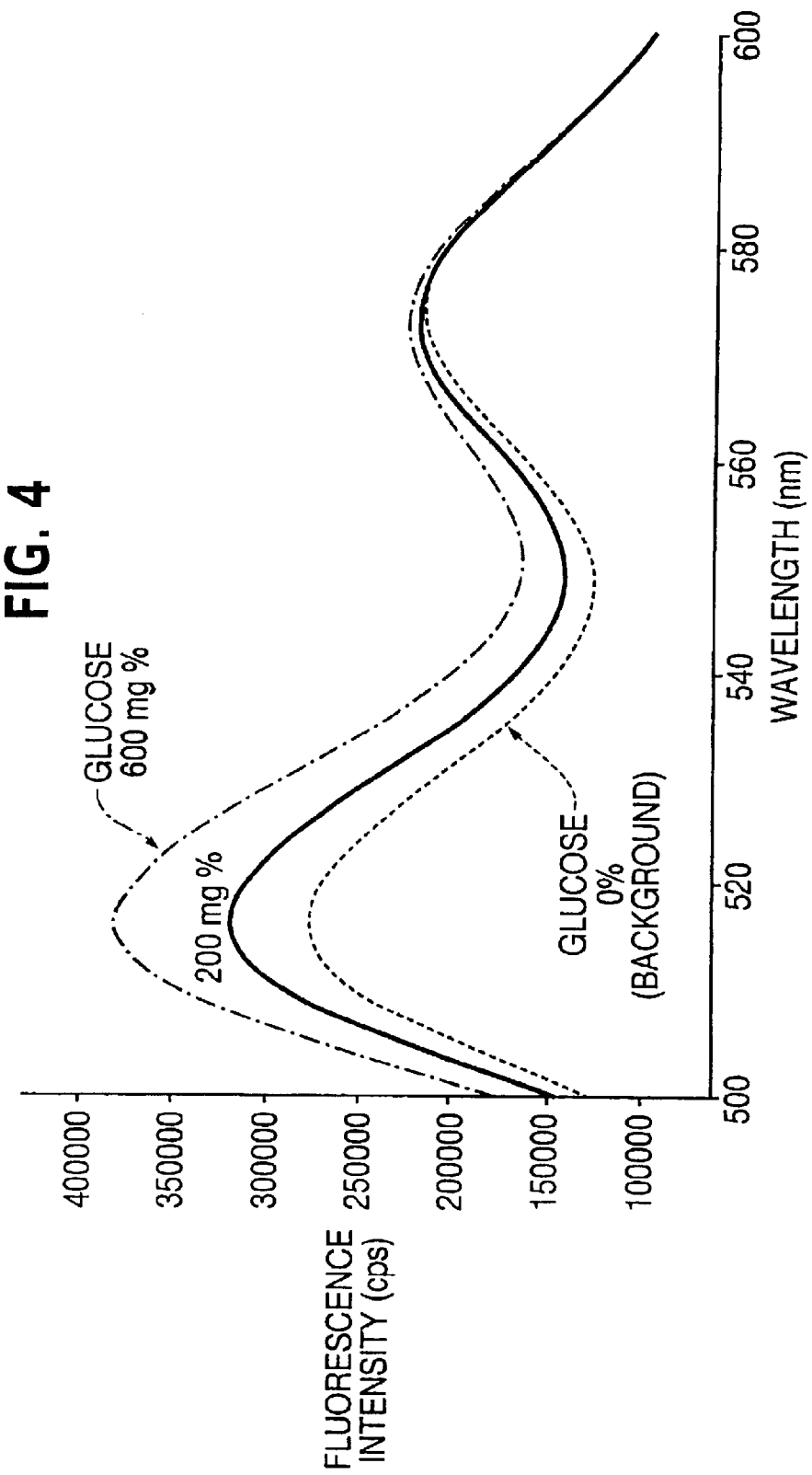

OCULAR ANALYTE SENSOR

This application is a continuation of U.S. patent application Ser. No. 09/784, 471, filed Feb. 15, 2001 now U.S. Pat. No. 6,681,127 which is a continuation in part of PCT application PCT/EP 00/08285 filed Aug. 24, 2000, which claims the benefits of U.S. provisional application Ser. No. 60/150,792 filed Aug. 26, 1999 and U.S. provisional application Ser. No. 60/185,980 filed Mar. 1, 2000.

An ophthalmic lens comprising a receptor moiety can be used to determine the amount of an analyte in an ocular fluid which is accessible to light. The receptor moiety can bind either a specific analyte or a detectably labeled competitor moiety. The amount of detectably labeled competitor moiety which is displaced from the receptor moiety by the analyte is measured and provides a means of determining analyte concentration in an ocular fluid, such as tears, aqueous humor, or interstitial fluid. The concentration of the analyte in the ocular fluid, in turn, indicates the concentration of the analyte in a fluid or tissue sample of the body that is not as accessible, such as blood or intracellular fluid.

Various noninvasive or minimally invasive methods to measure analytes, particularly glucose, have been described. For example, March, U.S. Pat. Nos. 3,958,560 and 4,014,321, discloses a glucose sensor wherein a patient's eye is automatically scanned using a source of light at one side of the cornea. A sensor located at the other side of the cornea detects the light that passes through the cornea. The level of glucose which rotates the plan of polarized light in the aqueous humor of the patient is a function of the amount of radiation detected. However, this sensor system is not necessarily specific or widely applicable to detection of analytes other than glucose, because it does not exploit the use of biological molecules which can detect glucose or other analytes in a body tissue or fluid sample. Biological molecules, as is well known, can provide very specific and sensitive detection reagents for particular analytes.

Schultz, U.S. Pat. No. 4,344,438, discloses a system for monitoring low molecular weight compounds in blood plasma by optical means, which involves a chamber which contains specific receptor sites for the plasma constituent to be analyzed. This system is very invasive, however, because it must be implanted within the blood stream using a hypodermic needle. The system also inherently contains the risks of clotting around the device, obstruction, and other adverse reactions, including immune reactions, general irritation, and foreign body reactions.

Embodiments of the present invention overcome these disadvantages in the prior art by employing an ophthalmic lens comprising a receptor moiety which comprises an analyte/competitor moiety binding site to detect an analyte in an ocular fluid. Concentration of a wide variety of analytes can be measured using an ophthalmic lens according to embodiments of the invention. Such analytes include, but are not limited to, electrolytes and small molecules (e.g., sodium, potassium, chloride, phenylalanine, uric acid, galactose, glucose, cysteine, homocysteine, calcium, ethanol, acetylcholine and acetylcholine analogs, ornithine, blood urea nitrogen, creatinine), metallic elements (e.g., iron, copper, magnesium), polypeptide hormones (e.g., thyroid stimulating hormone, growth hormone, insulin, luteinizing hormones, chorionogonadotrophic hormone), chronically administered medications (e.g., dilantin, phenobarbital, propranolol), acutely administered medications (e.g., cocaine, heroin, ketamine), small molecule hormones (e.g., thyroid hormones, ACTH, estrogen, cortisol, estrogen, and other metabolic steroids), markers of inflammation and/or allergy (e.g., histamine, IgE, cytokines), lipids (e.g., cholesterol), plasma proteins and enzymes (e.g., complement, coagulation factors, liver function enzymes, heart damage enzymes, ferritin), markers of infection (e.g., virus components, immunoglobulins such as IgM, IgG, etc., proteases, protease inhibitors), and/or metabolites (e.g., lactate, ketone bodies).

Ophthalmic lenses according to embodiments of the invention can be used to monitor the course of therapy or the level of disease in mammals, including primates and, preferably, humans. In addition, because ophthalmic lenses according to embodiments of the invention provide a way to detect analytes noninvasively, they provide distinct advantages over more traditional forms of monitoring such levels. Ophthalmic lenses according to embodiments of the invention also are useful for diagnostic purposes, for example to test for pregnancy (to detect β-HCG), to assess blood chemistry (electrolytes, $Ca_2PO_4$, magnesium, bilirubin, alkaline phosphatase, lactate dehydrogenase, alanine aminotransferase, etc.), and to detect infection (e.g., by detecting components of viruses such as CMV, EBV, hepatitis, and HIV, or bacteria, such as *Staphlococcus, Streptococcus*, etc.). They also are useful for monitoring blood levels of test compounds during the course of assessing the compounds for use as potential therapeutics.

Ophthalmic lenses according to embodiments of the invention can be worn chronically to provide repeated analyte measurements or can be worn for a single analyte measurement. Both qualitative and quantitative measurements can be performed.

BRIEF DESCRIPTION OF THE DRAWINGS

FIGS. 2A and 2B schematically show an analyte sensor system including an intraocular lens of the invention according to a preferred embodiment of the invention.

FIG. 4 shows the relationship between fluorescence intensity of an fluorescent intraocular lens of the invention at three glucose concentrations in vitro.

DETAILED DESCRIPTION OF THE INVENTION

Ophthalmic Lens

Figure 1:
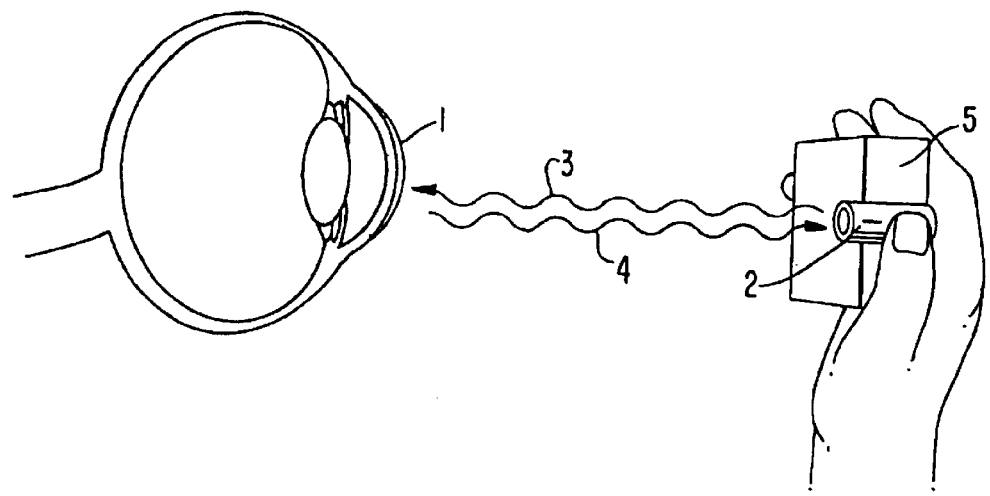
FIG. 1 schematically illustrates an analyte sensor system including a contact lens of the invention according to a preferred embodiment of the invention.
Figure 3A:
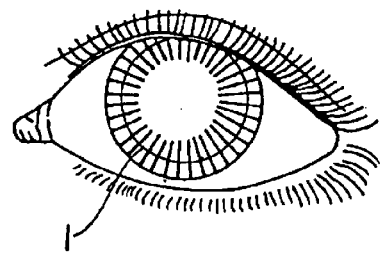
FIG. 3A schematically illustrates a contact lens of the invention as a analyte sensor.
Figure 3B:
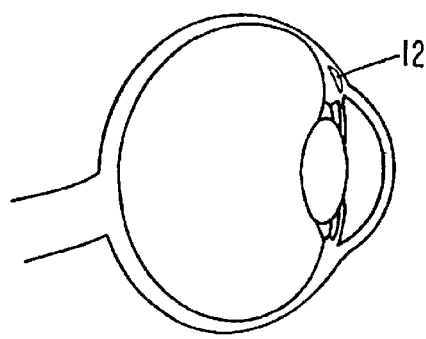
FIG. 3B schematically illustrates a subconjunctival lens of the invention as an analyte sensor.
Figure 3C:
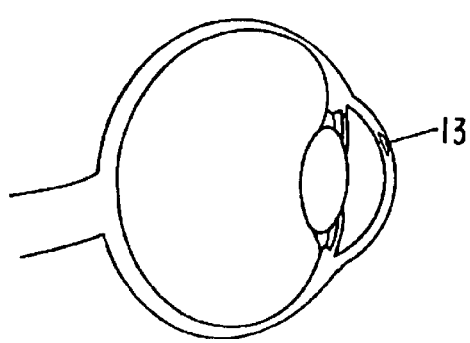
FIG. 3C schematically illustrates an intra-corneal lens of the invention as an analyte sensor.
Figure 1A:
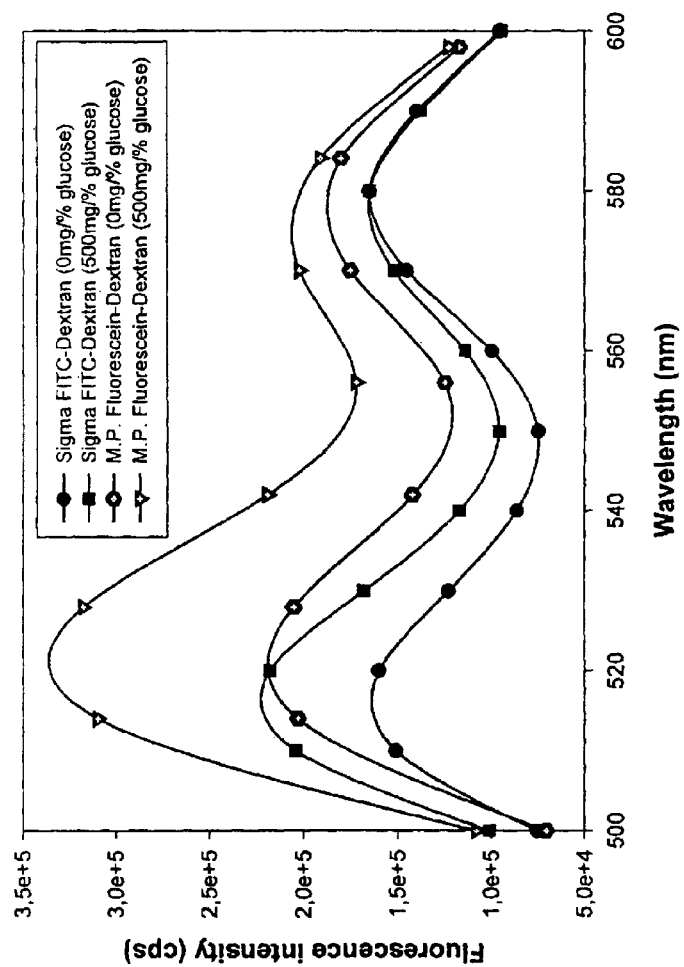
FIG. 1A schematically shows effects of fluorescein concentrations on the sensitivity of glucose detection using the fluorescein-dextran in a sensor.

An ophthalmic lens according to embodiments of the invention can be a removable lens, such as a contact lens, or a permanently implanted lens, such as an intraocular lens, a subconjunctival lens, or an intracorneal lens. See U.S. Ser. Nos. 60/150,792 and 60/185,980, the patent applications the priority of which is claimed for this invention. Permanently implanted lenses are particularly well-suited for use in individuals who have compromised ocular function (e.g., cataracts) and also have chronic conditions which require analyte measurement, such as diabetics.

Ophthalmic lenses can be corrective lenses or can be constructed so that they do not affect visual acuity. Contact lenses optionally can comprise a tint and are preferably disposable, which reduces the risk of infection for the user. As used herein, the term "ophthalmic lens" may also refer to a shunt or implant that may rest in the cul de sac of the eye.

Receptor Moiety

The ophthalmic lens comprises a receptor moiety. The receptor moiety comprises a binding site for the analyte to be detected. The binding site also binds a moiety which competes with the analyte for binding and is therefore referred to herein as an "analyte/competitor moiety binding site." Binding of both the competitor moiety and the analyte to the analyte/competitor moiety, binding site is reversible. The nature of the molecule used as the receptor moiety depends on the particular analyte to be detected, but minimally includes that portion of the molecule which is sufficient to contain an analyte/competitor moiety binding site.

For example, if glucose is the analyte to be detected, the receptor moiety preferably is concanavalin A (Mansouri & Schultz, *Bio/Tech* 2, 385, 1984), although other moieties, such as antibodies, boronic acid, a genetically engineered bacterial fluoriprotein, or glucose oxidase also can be used.

Boronic acid derivatives may also be used as competitive moieties for glucose, as they form covalent complexes with glucose. For example, a combination of a fluorescence moiety, such as anthracene, boronic acid and tertiary amine gives a sensor for glucose. Illustrative, but none limiting boronic acid compounds are listed below:

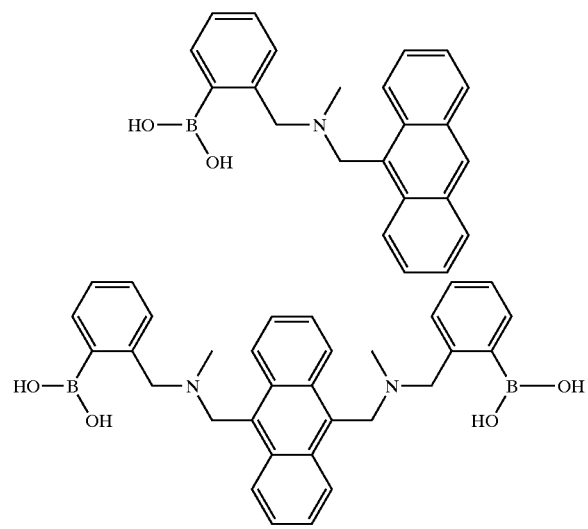

Glucose binds with the acidic boronic moiety creating a fluorescent moiety.

f phenylalanine is the analyte to be detected, the receptor moiety preferably comprises the active site of phenylalanine hydroxylase. It is well within the skill of those knowledgeable in the art to determine other analyte-receptor moiety binding pairs, such as uric acid-uricase, alcohol-alcohol dehydrogenase, copper-ceruloplasmin, galactose-galactokinase, cysteine- and/or homocysteine-cystathionine synthetase, acetylcholine-acetylcholinesterase, ornithine-diamine oxidase, and the like.

Competitor Moiety

For use in detecting an analyte, an ophthalmic lens according to embodiments of the invention preferably comprises a competitor moiety having a detectable label. The competitor moiety competes with the analyte for binding to the analyte/competitor moiety binding site. The detectable label can intrinsically be part of the competitor moiety. Alternatively, the detectable label can be a label which is not naturally associated with the competitor moiety but which is attached by means of a chemical linkage, such as a covalent bond. In preferred embodiments, the competitor moiety comprises a fluorescent label. Other detectable labels, such as luminescent or calorimetric labels, also can be used.

Again, it is well within the skill of those in the art to select a competitor moiety which will compete with an analyte for binding to a particular analyte/competitor moiety binding site. For example, competitor moieties which can be used with the analyte-receptor moiety binding pairs disclosed above include fluorescein dextran (which competes with glucose for binding to concanavalin A), fluorescein polyglutamylurate (which competes with uric acid for binding to uricase), fluorescein nanolol (which competes with alcohol for binding to alcohol dehydrogenase), fluorescein-glutamine phenylacetate (which competes with phenylalnine for binding to phenylalanine hydroxylase), fluorescein-erythrocuprein (which competes with copper for binding to ceruloplasmin), fluorescein-2,3,6-tri-O-methyl galactose (which competes with galactose for binding to galactokinase), fluorescein-S-adenosyl polyhomocysteine (which competes with cysteine and homocysteine for binding to cystathionine synthetase), fluoropolyglutamyl prostigmine (which competes with acetylcholine for binding to acetylcholinesterase), and fluorospermine (which competes with ornithine for binding to diamine oxidase).

Most preferably, the detectable label is more readily detectable when the competitor moiety is not bound to the analyte/competitor moiety binding site. Thus, fluorescent labels, such as fluorescein, indocyanine green, malachite green, and rhodamine, which are quenched when the competitor moiety is bound but are unquenched when the competitor moiety is not bound, are preferred for use in ophthalmic lenses according to embodiments of the invention.

In addition, the sensitivity of the monitor can be controlled by altering the concentration of the detectable label. For example, the free resonance energy transfer function, an indicator of measurement sensitivity, can be increased by increasing the concentration of the detectable, label. Thus in the case of fluorescein dextran (which competes with glucose for binding to concanavalin A), increasing the concentration of fluorescein on the competitive moiety increases the range of fluorescence intensity. Increasing the range of fluorescence intensity increases the sensitivity of resulting measurements.

The principle is illustrated in FIG. 14. Two different fluorescein dextran compounds, each with differing fluorescein concentrations, were tested in the same glucose environments and the fluorescence intensity measured. Sigma FITC-Dextran has a fluorescein concentration of 2% and M.P. Fluorescein-Dextran has a fluorescein concentration of 4%. Each solution was measured in a fluorophotometer with variable wavelength. The first peak is characteristic of fluorescein, the second of rhodamine. As can be seen from FIG. 1, M.P. Fluorescein-Dextran, the compound with the higher fluorescein concentration has a greater range of fluorescence intensity as measured at a given wavelength than the Sigma FITC-Dextran. The larger range of fluorescence gives greater sensitivity when measuring patient glucose levels.

It is important to note the purity of the competitive moiety can influence the activity level of the detectable label. For example, in the case of fluorescein dextran, the relative level of monomers, dimers or tetramers can influence the sensitivity. Relatively pure levels of dimers seem to positively influence sensitivity.

Providing Receptor and Competitor Moieties in an Ophthalmic Lens

A variety of options are available for providing the receptor and competitor moieties in an ophthalmic lens. Construction of various types of ophthalmic lenses is well known in the art. Construction of contact lenses is taught, for example, in U.S. Pat. Nos. 5,965,631, 5,894,002, 5,849,811, 5,807,944, 5,776,381, 5,426,158, 4,099,859, 4,229,273, 4,168,112, 4,217,038, 4,409,258, 4,388,164, 4,332,922, 4,143,949, 4,311,573, 4,589,964, and 3,925,178.

Construction of intraocular lens implants is taught, inter alia, in U.S. Pat. Nos. 6,051,025, 5,868,697, 5,762,836, 5,609,640, 5,071,432, 5,041,133, and 5,007,928. Subconjunctival lenses are taught, for example, in U.S. Pat. Nos. 5,476,511, 5,400,114, and 5,127,901. Intracorneal lenses are taught, inter alia, in U.S. Pat. Nos. 6,090,141, 5,984,961, 5,123,921, and 4,799,931.

In one embodiment, the receptor moiety is covalently bound to the ophthalmic lens material. In another embodiment, the ophthalmic lens comprises a polymer meshwork containing pores. The pores are of a size which permit the competitor moiety to bind reversibly to the analyte/competitor moiety binding site, but which prevent the receptor moiety and the competitor moiety from diffusing out of the ophthalmic lens. Suitable polymers for this purpose are known in the art and include hydrogels, such as stable polymers of polyethylene glycol hydrogel (PEGH) (March et al., 2000), and modified polyvinylalcohol, such as nelfilcon A.

In another embodiment, the ophthalmic lens comprises a receptor moiety layer, a polyelectrolyte layer, and a competitor moiety layer. The polyelectrolyte layer includes one or more polyelectrolytes, which are generally high molecular weight polymers with multiple ionic or ionizable functional groups. At least one polyelectrolyte in the polyelectrolyte layer has a charge opposite to the overall charge of the receptor moiety and competitor moiety layers. Suitable polyelectrolytes include positively charged PDDA (polydiallyldimethylammonium chloride) and negatively charged PAA (polyacrylic acid). Assembly of the layers is based upon sequential adsorption of oppositely charged polyions. The sensor and spacing polyelectrolytes are deposited as uniform thin films (1–10 nm) in 10–15 deposition cycles onto the porous polyvinyl alcohol or hydrogen matrix, resulting in only a 100–500 nm thick coating for the sensing film, which is highly biocompatible. A typical sequence for construction of an ophthalmic lens suitable for glucose detection involves a deposition cycle of ultrathin (1–10 nm) films of PDDA, PM, PDDA, concanavalin A, PDDA, PM, PDDA, fluorescein dextran, PDDA, PM, PDDA, PAA, concanavalin A, PM, fluorescein dextran, PM, etc. Technology for constructing ophthalmic lenses comprising such layers is taught, for example, in WO 99/35520.

An ophthalmic lens according to embodiments of the invention can be provided in a kit, together with instructions for measuring analyte concentration as described below. The invention provides kits which are intended for individual patient use, in which the ophthalmic lens typically is a contact lens, as well as kits for medical practitioners, which can comprise any of the ophthalmic lenses or their equivalents described herein.

Analyte Sensor System

An ophthalmic lens according to embodiments of the invention can be used in an analyte sensor system. The analyte sensor system comprises an ophthalmic lens and a detector configured to detect the detectable label. For example, if the label is a luminescent label, the detector may include a luminometer; if the label is a colorimetric label, the detector may include a colorimeter; if the label is a fluorescent label, the detector may include a fluorophotometer. Construction of such devices is well known in the art. Light with wavelengths which will excite the fluorescent label can be provided, for example, by a laser or a light source, such as a light-emitting diode. A fluorophotometer suitable for use with embodiments of the invention can be constructed using a light-emitting diode from Power Technology, Inc. (Little Rock, Ark.) (see March et al., *Diabetes Technol. & Ther.* 2, 27–30, 2000).

The detector can be a free-standing device, a table-top device, or a hand-held device. For convenience, the detector can be a miniaturized device and may be worn or carried as a personal accessory, for example, mounted in the frame of a pair of eyeglasses, clipped to an article of clothing, such as a shirt or sweater, hung around the neck, worn around the wrist, or clipped to a belt or a key ring.

Using an ophthalmic lens in an analyte sensor system, as described above, embodiments of the invention provides methods of measuring analyte concentration in an ocular fluid. This measurement can, in turn, be manipulated to provide a measurement of the analyte's concentration in a body tissue or a fluid, such as blood or intracellular fluid. The relationship between glucose concentration in the aqueous humor and the blood, for example, is well known. See Süllmann, in HANDBUCH DER PHYSIOLOGISCHEN CHEMIE, Vol. II/a, p. 867 ff., Springer, Berlin, 1956; Graymore, in THE EYE, Vol. 1, p. 348, Davson, ed., Academic Press, NY, 1962; De Berardinis et al., *Exp. Eye Res.* 4, 179, 1965; Pohjola, *Acta Ophthalmologica Suppl.* 88, 1966; Reim et al., *Ophthalmologica* 154, 39–50, 1967; Kinsey & Reddy, in Prince, ed., THE RABBIT AND EYE RESEARCH, C. C. Thomas, Springfield, Ill., 1964, p. 218. The relationship between the concentration of another analyte in a body tissue or fluid and the concentration of the analyte in an ocular fluid can be determined by methods well known in the art. See, for example, March et al., *Diabetes Care* 5, 259–65, 1982. The detector can be configured to convert the measurement of the analyte concentration into a value which reflects the concentration of the analyte in the relevant body tissue or fluid, e.g., blood.

If desired, the analyte sensor system also can comprise a transmitter configured to transmit a signal representing whether the detectable label is detected and/or an amount of the detectable label that is detected. A device configured to vary the concentration of the analyte in a body fluid or tissue, such as an infusion pump or other pump, may receive the signal and may vary the concentration response to the signal. The signal from the analyte sensor system may comprise a continuous or discontinuous telemetry signal generated by the detector. The pump may, in response to the signal, adjust the levels of the analyte in the body by providing the user with the appropriate amount of a regulator moiety, such as insulin. Infusion pumps are well known in the art for delivering a selected medication to a patient including humans and other animals in accordance with an administration schedule which can be preselected or, in some instances, preprogrammed. Pumps for use in this invention can be worn externally or can be directly implanted into the body of a mammal, including a human, to deliver a specific medication such as insulin to the mammal in controlled doses over an extended period of time. Such pumps are well known and are described, for example, in U.S. Pat. Nos.

5,957,890, 4,923,375, 4,573,994, and 3,731,681. Medications which should optimally be maintained at a constant level, such as phenobarbital, baclofen, theophylline, and cardiac and blood pressure medications, also can be provided by means of an infusion pump.

Illustrative Embodiments

Illustrative embodiments of the analyte sensor system according to embodiments of the invention are shown in FIGS. 1 and 2. FIG. 1 is a schematic view of an analyte sensor system employing a contact lens 1, a radiation detector 5, such as a fluorophotometer, and a radiation source 2, such as a laser (which preferably is of low power) or light emitting diode, which emits light 3 with a first wavelength which will excite the fluorescent label in competitor moieties contained within the contact lens 1. In response to the light 3, competitor moieties which are not bound to receptor moieties will thereby emit light 4 of a second different wavelength (e.g., by fluorescence), which can be detected and measured by a radiation detector 5. The radiation detector 5 and the radiation source 2 may be embodied together as a hand-held unit, as shown in FIG. 1.

Figure 2C:
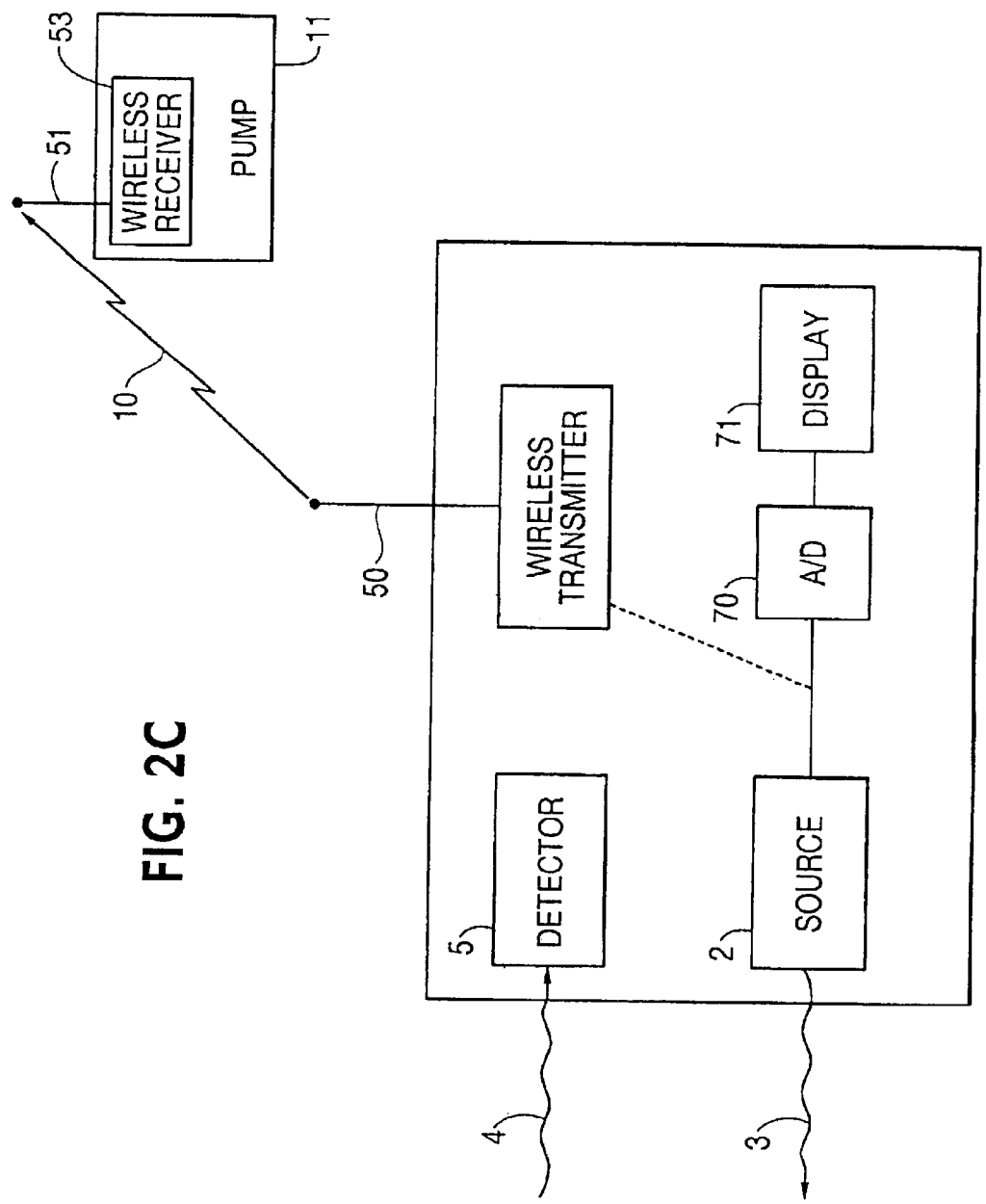
FIG. 2C is schematic flow chart of signal transmission in an analyte sensor system of the invention according to a preferred embodiment.

Conveniently, a miniaturized version of the radiation source 2 and the radiation detector 5 can be configured to be built into a pair of eyeglasses. An exemplary embodiment of this is shown in FIGS. 2A and 2B. The analyte sensor system shown in FIGS. 2A and 2B employs an intraocular lens 8, which comprises a polymer 9 containing receptor moieties and fluorescently labeled competitor moieties. A light-emitting diode 6 is mounted in the frame of a pair of eyeglasses 7. The light-emitting diode 6 emits light 3 with a first wavelength which will excite the fluorescent label in the competitor moieties. Competitor moieties which are not bound to receptor moieties will thereby emit light 4 of a second different wavelength, which can be detected and measured by a fluorophotometer 5, which is mounted together with the light-emitting diode 6 in the eyeglasses frame 7. A telemetry signal 10 is transmitted to an infusion pump 11, which can provide a regulator moiety, such as insulin, to maintain suitable levels of the analyte in the body. The telemetry signal 10 may be analog or digital and may be transmitted via wire or cable, such as wire 60, or wirelessly, such as via radio frequency or infrared transmission. Where the telemetry signal 10 is transmitted wirelessly, the analyte sensor system may include antennas 50, 51, for such wireless transmission. Antenna 50 may, if desired, be embedded within eyeglass frame 7. As shown in FIG. 2C, the antennas 50, 51 may be coupled with a respective wireless transmitter 52 and wireless receiver 53.

The telemetry signal 10 may include qualitative information as to whether or not the analyte is detected by the radiation detector 5. For example, where the detected light 4 is at or exceeds a predetermined threshold, the telemetry signal 10 may represent a "detected" state (such as the existence of telemetry signal 10). Where the detected light 4 is below the threshold, the telemetry signal 10 may represent a "not detected" state (such as the absence of telemetry signal 10). Alternatively, the telemetry signal 10 may indicate a change in analyte concentration. Telemetry signal 10 also may provide a warning signal if the analyte concentration is above or below a preset range.

Optionally, the telemetry signal 10 may include quantitative information as to how much light 4 is detected by the radiation detector 5. For instance, the telemetry signal 10 may be varied in amplitude and/or frequency responsive to the amount of light 4 detected, where the amplitude and/or frequency represents the amount of light 4. As another example, the telemetry signal 10 may include digital data representing the amount of detected light 4.

If the telemetry signal 10 is analog, the telemetry signal 10 may be generated by the detector 5, which may include a modulator for generation of the telemetry signal 10. If the telemetry signal 10 is digital, the telemetry signal 10 may be generated by an analog-to-digital ("A/D") converter 70. Also, the amount of the light 4 detected by the radiation detector 5 may be shown on a display 71 (which may include a display driver), such as a CRT screen or liquid crystal display ("LCD").

All patents and patent applications cited in this disclosure are expressly incorporated herein by reference. The above disclosure generally describes the present invention. A more complete understanding can be obtained by reference to the following specific examples which are provided for purposes of illustration only and are not intended to limit the scope of the invention.

EXAMPLE 1

Construction of an Intraocular Glucose Sensor

A structurally stable polymer of polyethylene glycol hydrogel (PEGH, Shearwater Polymers, Inc.) is used to construct an intraocular glucose sensor. PEGH is immobilized in an intraocular lens (Alcon Laboratories, 6 mm circumference, 1 mm thickness). Chemically immobilized pendant tetramethylrhodamine isothiocyanate concanavalin A (TRITC-ConA, Sigma) is incorporated into the PEGH as the receptor moiety and fluorescein isothiocyanate dextran (FITC-dextran, Sigma) is incorporated as the competitor moiety by polymerization under UV light, as described by Ballerstadt & Schultz, Anal. Chim. Acta 345, 203–12, 1997, and Russell & Pishko, Anal. Chem. 71, 3126–32, 1999. While the FITC-dextran is bound to the TRITC-ConA, the FITC fluorescence is quenched via a fluorescence resonance energy transfer. Increased glucose concentration frees the FITC-dextran and results in fluorescence which is proportional to glucose concentration.

FIG. 4 shows the relationship between fluorescence intensity of our fluorescent intraocular lens at three glucose concentrations in vitro. A linearly proportional relationship occurs between 0 and 500 mg % at 518 nm, which is the peak of fluorescein fluorescence. The peak at 575 nm is due to the rhodamine in the TRITC-ConA.

EXAMPLE 2

Implantation of an Intraocular Glucose Sensor In Vivo

The intraocular lens glucose sensor described in Example 1 is implanted into the anterior chamber of the eye of a living New Zealand rabbit with a blood glucose concentration of 112 mg %. The implant is visible as a bright spot of green fluorescence (518 nm) within the eye. Careful examination with a biomicroscope slit lamp shows no sign of toxicity, rejection, or any reaction 6 months after implantation.

What is claimed is:

1. An ophthalmic sensor for detecting an analyte in an ocular fluid, comprising:
    an ophthalmic lens; and
    one or more detection reagents for said analyte in and/or on said ophthalmic lens, wherein the detection reagents comprise a receptor moiety and a fluorescent moiety wherein the receptor moiety comprises an analyte/competitor moiety binding site at which the analyte can reversibly bind, and wherein the fluorescent moiety in cooperation with the receptor moiety provides a detection of the analyte.

2. The ophthalmic sensor of claim 1, wherein the opthalmic lens is selected from the group consisting of a contact lens, an intraocular lens, a subconjunctival lens, an intracorneal lens, and a shunt or implant that can rest in the cul de sac of an eye.

3. The ophthalmic sensor of claim 2, wherein the analyte is selected from the group consisting of an electrolyte, a metallic element, a polypeptide hormone, a chronically administered medication, an acutely administered medication, small molecule hormone, a marker of inflammation, a marker of allergy, a lipid, a protein, marker of infection, and a metabolite.

4. The ophthalmic sensor of claim 3, wherein the ocular fluid is selected from the group consisting of tears, aqueous humor, and interstitiial fluid.

5. The ophthalmic sensor of claim 2, wherein the detection reagents are covalently bound to the lens material of the ophthalmic lens.

6. The ophthalmic sensor of claim 5, wherein the detection reagents are boronic acid derivatives.

7. The ophthalmic sensor of claim 6, wherein the boronic acid derivatives comprise a fluorescent moiety, a boronic acid and tertiary amine.

8. The ophthalmic sensor of claim 2, wherein the detection reagents are boronic acid derivatives.

9. The ophthalmic sensor of claim 8, wherein the boronic acid derivatives comprise a fluorescent moiety, a boronic acid and tertiary amine.

10. An analyte sensor system, comprising
   (a) an ophthalmic lens for detecting an analyte in an ocular fluid, having detection reagent for said analyte, wherein the detection reagent comprises a receptor moiety and a fluorescent moiety, wherein the receptor moiety comprises an analyte/competitor moiety binding site at which the analyte can reversibly bind, and wherein the fluorescent moiety in cooperation with the receptor moiety provides a detectable signal indicative of the analyte;
   (b) a detector configured to detect the detectable signal.

11. The analyte sensor system of claim 10, further comprising a transmitter coupled to the detector and configured to transmit to a pump a signal indicating whether the detectable signal is detected by the detector, wherein the pump is configured to vary a concentration of the analyte in a body fluid or tissue.

12. The analyte sensor system of claim 11, wherein the transmitter is contained in a personal accessory.

13. The analyte sensor system of claim 11, further comprising the pump.

14. The analyte sensor system of claim 11, wherein the transmitter is further configured to transmit the signal to the pump wirelessly.

15. The analyte sensor system of claim 10, wherein the ophthalmic lens is selected from the group consisting of a contact lens, an intraocular lens, a subconjunctival lens, an intracorneal lens and a shunt or implant that can rest in the cul e sac of an eye.

16. The analyte sensor system of claim 15, wherein the analyte is glucose and the body fluid is blood.

17. The ophthalmic sensor of claim 15, wherein the detection reagent is covalently bound to the lens material of the ophthalmic lens.

18. The ophthalmic sensor of claim 17, wherein the detection reagent is a boronic acid derivative.

19. The ophthalmic sensor of claim 18, wherein the boronic acid derivative comprises a fluorescent moiety, a boronic acid and tertiary amine.

20. A kit for detecting glucose in an ocular fluid, comprising:
   a contact lens comprising a boronic acid derivative which can bind reversibly to glucose to provide a fluorescent signal; and
   instructions for using the contact lens to detect glucose in the ocular fluid.

21. The kit of claim 20, wherein the boronic acid derivative comprises a fluorescent moiety, a boronic acid and tertiary amine.

22. The kit of claim 20, comprising a detector for detecting the fluorescent signal.

* * * * *